US005529898A

United States Patent [19]
Rogers et al.

[11] Patent Number: 5,529,898
[45] Date of Patent: Jun. 25, 1996

[54] METHODS OF DETECTING DISORDERS OF THE CENTRAL NERVOUS SYSTEM BY DETECTING AUTOANTIBODIES WHICH SPECIFICALLY BIND IONOTROPIC GLUTAMATE RECEPTORS

[75] Inventors: Scott W. Rogers, Salt Lake City, Utah; James O. McNamara, Sr., Chapel Hill, N.C.; Stephen F. Heinemann, La Jolla, Calif.

[73] Assignees: Duke University, Durham, N.C.; The Salk Institute for Biological Studies, La Jolla, Calif.

[21] Appl. No.: 109,234

[22] Filed: Aug. 19, 1993

[51] Int. Cl.$^6$ .......................... G01N 33/53; G01N 33/564
[52] U.S. Cl. .......................... 435/7.1; 435/7.92; 435/7.93; 435/7.94; 435/7.95; 436/506; 436/811
[58] Field of Search ..................... 435/7.92, 7.9, 435/7.93, 7.94, 7.95; 436/506, 811

[56] References Cited

U.S. PATENT DOCUMENTS

| 4,747,952 | 5/1988 | Nakano et al. | 210/650 |
|---|---|---|---|
| 4,925,787 | 5/1990 | Tanihara et al. | 435/7.5 |

FOREIGN PATENT DOCUMENTS

| 0558747A1 | 9/1993 | European Pat. Off. . |
| 9300586 | 1/1993 | WIPO . |

OTHER PUBLICATIONS

H. L. Weiner et al., *Double–Blind Pilot Trial of Oral Tolerization with Myelin Antigens in Multiple Sclerosis* Science 259, 1321–1324 (1993).

*Current Practice in Therapeutic Plasmapheresis Proceedings of two symposia held at the 17th International Congress of Internal Medicine*, Kyoto, Oct. 11, and 12, pp. 158–177 (1984).

*Plasma Exchange Therapy in Neurological Disorders: A Clinician's Overview, Therapeutic Hemapheresis II* pp. 27–54 CRC Press, 1985.

*Apheresis in the Treatment of Neurological Diseases, Therapeutic Apheresis* Chapter 4, pp. 35–58 (1983), American Association of Blood Banks.

W. G. Honer et al., *Characterization of a Synaptic Antigen of Interest in Neuropsychiatric Illness Biol. Psychiatry* 31, 147–158 (1992).

D. W. Choi, *Glutamate Neurotoxicity and Diseases of the Nervous System Neuron* 1(8)623–634, 1988.

J. O. McNamara and Inwin Fridovich, *Did Radicals Strike Lou Gehrig Nature*, pp. 20–22 (1993).

R. Dingledine et al., *Excitatory amino acid receptors in epilepsy TIPS* 11, pp. 334–338 (1990).

G. P. Gasic and Michael Hollmann, *Molecular Neurobiology of Glutamate Receptors Annu. Rev. Physiol.* 54, 507–536 (1992).

M. Barinaga; *Antibodies Linked to Rare Epilepsy, Science* 268, pp. 362–363 (21 Apr. 1995).

R. E. Twyman et al; *Glutamate Receptor Antibodies Activate a Subset of Receptors and Reveal on Agonist Binding Site, Neuron* 14, pp. 755–762 (Apr. 1995).

Gorman et al., "Humanisation of monoclonal antibodies for therapy" *Immunology*, vol. 2 pp. 457–466 (1990).

Rogers S. W. et al. "Autoantibodies to Glutamate Receptor GluR3 in Rasmussen's Encephalitis". *Science* 265:648–651, 1994.

Ettlinger, G. and Lowrie, M. B. "An Immunological Factor in Epilepsy," *The Lancet* (i) 1386, 1977.

Piatt J. H. et al. "Chronic Focal Encephalitis (Rasamussen Syndrome): Six Cases". *Epilepsia* 29(3) 268–279, 1988.

Bouma, P. A. D. "Determining the Prognosis of Childhood Epilepsy by Establishing Immune Abnormalities," *Clinical Neurology and Neurosurgery* 94 (Suppl.): 554–556, 1992.

*Primary Examiner*—Toni R. Scheiner
*Assistant Examiner*—Patricia A. Duffy
*Attorney, Agent, or Firm*—Bell, Seltzer, Park & Gibson

[57] ABSTRACT

A method of screening a subject for a central nervous system disorder caused by autoimmune disease (e.g., an inflammatory seizure disorder) comprises a sample from the subject and then detecting the presence or absence of anti-glutamate receptor autoantibodies (e.g., anti-GluR3 glutamate receptor autoantibodies) in the biological sample. The presence of such autoantibodies indicates the subject is afflicted with a central nervous system disorder caused by autoimmune disease. Methods of treating such disease by reducing the number of autoantibodies available to bind to glutamate receptors in the subject are also disclosed.

15 Claims, 1 Drawing Sheet

METHODS OF DETECTING DISORDERS OF THE CENTRAL NERVOUS SYSTEM BY DETECTING AUTOANTIBODIES WHICH SPECIFICALLY BIND IONOTROPIC GLUTAMATE RECEPTORS

This invention was made with Government support under Grant Numbers NS17771 and NS30990R29 from the National Institutes of Health. The Government has certain rights to this invention.

FIELD OF THE INVENTION

This invention relates to methods of detecting and treating disorders of the central nervous system which involve autoantibodies directed against glutamate receptors.

BACKGROUND OF THE INVENTION

The first neuromuscular disorder for which plasma exchange was suggested as a treatment was myasthenia gravis. Since that time, plasma exchange has been attempted on several other neurological diseases, including Eaton-Lambert myasthenic syndrome, polymyositis, dermatomyositis, acute Guillain-Barre syndrome, chronic Guillain-Barre syndrome, multiple sclerosis, Refsum's disease, Amyotrophic lateral sclerosis, hyperviscosity coma, and polyneuropathy. Results have for various of these treatments have been characterized as positive, equivocal, doubtful, and negative. See P. Reuther, Plasma Exchange Therapy in Neurological Disorders: A Clinician's Overview, in *Therapeutic Hemapheresis*, vol. 2, pgs 27–54 (J. MacPherson and D. Kasprisin Eds. 1985); see also *Current Practices in Therapeutic Plasmapheresis*, pgs 158–177 (Y. Shiokawa and N. Inoue Eds. 1985); *Therapeutic Apheresis*, pgs. 35–58 (J. Kolins and J. Jones Eds. 1983); H. Weiner, *Science* 259, 1321 (26 Feb. 1993).

For myasthenia gravis, it is generally accepted that anti-acetylcholine receptor antibodies are the underlying pathologic factors which are removed by plasma exchange. For most of the other nervous system diseases treated by plasma exchange, the underlying etiology is unknown. However, without a knowledge of the underlying mechanism of the disease, it is difficult to monitor antibody levels in conjunction with plasma exchange so that treatment may be appropriately administered. Accordingly, there is a continued need for greater understanding of the autoimmune mechanisms underlying nervous system disorders.

SUMMARY OF THE INVENTION

The present invention is based on the observation that, when rabbits are immunized with certain glutamate receptor proteins, those rabbits develop a disorder remarkably similar to human Rasmussen's encephalitis. This indicates that an autoimmune process directed against glutamate receptors is pathogenic.

Accordingly, a first aspect of the present invention is a method of screening a subject for a central nervous system disorder caused by autoimmune disease. The method comprises the steps of collecting a biological sample from the subject, and then detecting the presence or absence of anti-glutamate receptor autoantibodies in the biological sample. The presence of autoantibodies indicates the subject is afflicted or likely to be afflicted with a central nervous system disorder caused by autoimmune disease.

A second aspect of the present invention is a method of combatting a central nervous system disorder caused by autoimmune disease. The method comprises selectively reducing (e.g., by selective immunoabsorption) the amount of anti-glutamate receptor autoantibodies in the subject which are available to bind to glutamate receptors in the subject, the reduction being sufficient to combat the disorder.

A third aspect of the present invention is a also method of combatting a central nervous system disorder caused by autoimmune disease in a subject in need of such treatment. The method comprises, first, reducing (e.g., by plasma exchange or plasmapheresis) the amount of anti-glutamate receptor autoantibodies in said subject available to bind to glutamate receptors in said subject, then collecting a biological sample from said subject, and then detecting the amount of anti-glutamate receptor autoantibodies in said biological sample. Then, if the amount of anti-glutamate receptor autoantibodies is determined to be insufficiently reduced in said subject to combat said disease, the step of reducing the amount of anti-glutamate receptor autoantibodies is repeated.

The foregoing and other objects and aspects of the present invention are explained in detail in the drawings herein and the specification set forth below.

DETAILED DESCRIPTION OF THE INVENTION

Figure 1:
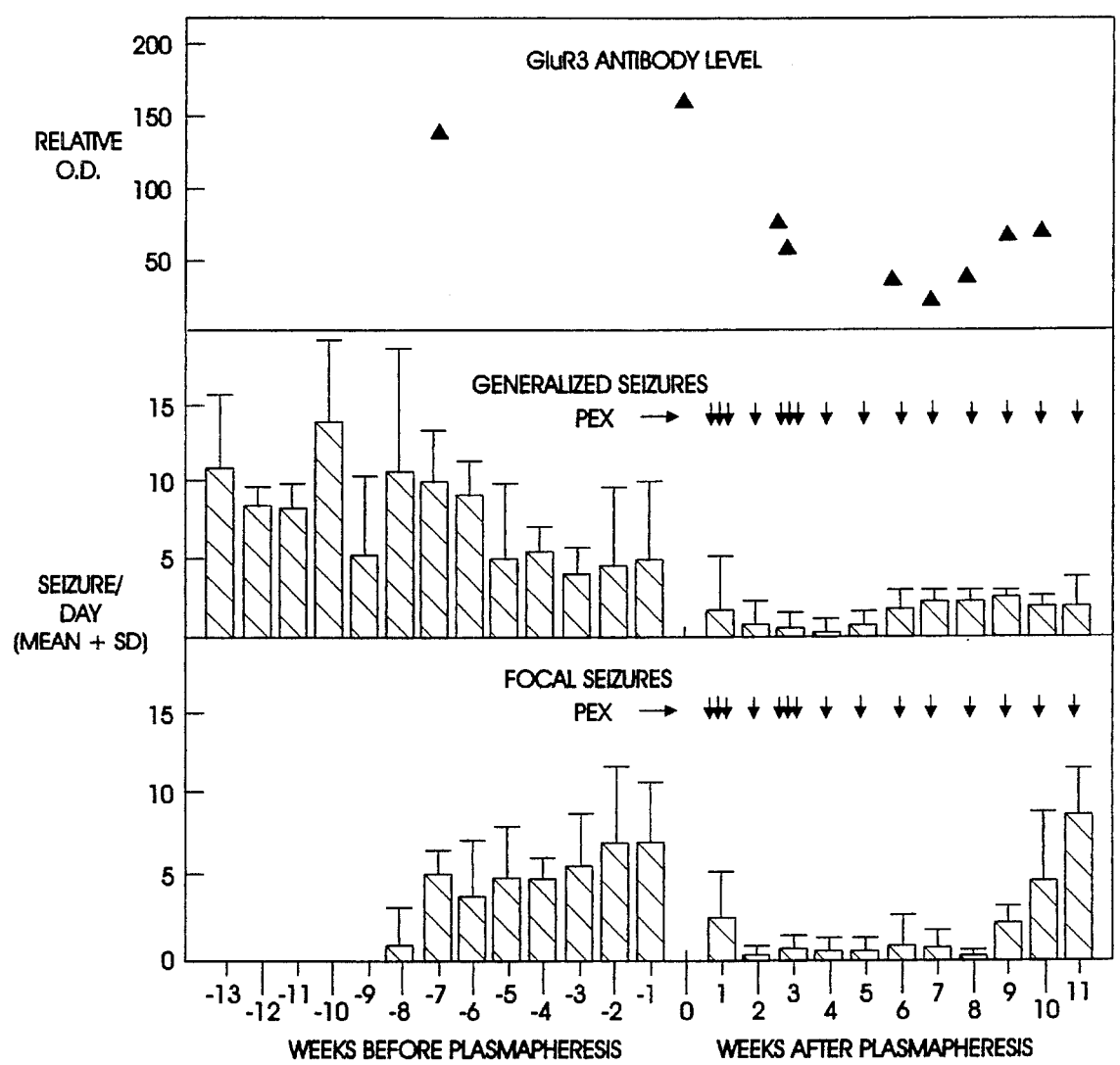
FIG. 1 shows the effects of plasma exchange on a human female patient afflicted with Rasmussen's encephalitis. The top panel presents the results of GluR3 antibody titers determined by ELISA in the patient, as measured in Relative Optical Density (Relative O.D.). The middle and lower panels present the frequency of generalized and partial seizures, respectively, before and after the initiation of plasma exchange (PEX).

Patients to be screened and treated by the methods of the present invention include human patients afflicted or suspected of being afflicted with Rasmussen's encephalitis. Rasmussen's encephalitis is a syndrome of progressive unilateral brain dysfunction and intractable focal seizures which affects otherwise normal children. Unihemispheric dysfunction progresses relentlessly in both severity and extent over a period of months to decades, culminating in hemiparesis and dementia. The main pathological findings are: leptomeningeal lymphocytic infiltrates, perivascular lymphocytic cuffing, multiple microglial nodules in the cortex, neuronophagia, neuronal loss, gliosis and spongiosis. Enigmatically the characteristic inflammatory histopathologic abnormalities are restricted to the cortex of one cerebral hemisphere. Treatment of the incapacitating seizures with conventional anticonvulsants is of little benefit. Seizures may be temporarily controlled by partial corticectomies, but spread of the process to the rest of the hemisphere eventually follows. Defunctioning hemispherectomy is the recommended alternative despite the inevitable consequences of hemiplegia and profound hemispheric dysfunction.

The present invention is also applicable to detecting and treating other seizure disorders, particularly inflammatory seizure disorders, in addition to those formally classified as Rasmussen's encephalitis, when autoimmunity to glutamate receptors is an underlying cause thereof. For example, among patients with temporal lobe epilepsy undergoing hippocampal resection for treatment, specimens removed from approximately 5% of these patients exhibit inflammatory pathogenic changes in the brain tissue, as seen in Rasmussen's encephalitis.

In addition to seizure disorders, those skilled in the art will appreciate that glutamate receptors are involved in a variety of different functions in the central nervous system, and that the present invention is, therefore, generally applicable to the treatment of disorders of the central nervous system involving autoimmunity to glutamate receptors regardless of the particular disorder manifested. For example, it is contemplated that the present invention is also applicable to some forms of sporadic amyotrophic lateral sclerosis (ALS) due to an autoimmune mechanism directed at glutamate receptors. The histopathology of sporadic ALS discloses findings similar to that of Rasmussen's encephalitis but the abnormalities are found in the anterior portion of the spinal cord, motor cortex, and cortico-spinal tracts. In addition, it is known that the treatment of experimental animals with homogenates of the anterior portion of the spinal cord mixed with Freund's adjuvant produces a syndrome resembling ALS (though the nature of the antigen has heretofore been unclear). A pathologic immune response directed against glutamate receptors may also contribute to some forms of Alzheimer's disease. The idea that an immune mechanism contributes to the pathophysiology of Alzheimer's disease is based upon the fact that inflammatory changes are frequently found in the brains of patients with Alzheimer's disease. Moreover, treatment of patients with Alzheimer's disease with anti-inflammatory drugs appears to slow the progression of the disease. See *Science* 260, 1719–1720 (1993). In addition, a dopamine autoimmune mechanism has previously been suggested to underlie some forms of schizophrenia. D Kirch, *Schizophrenia Bulletin* 19, 355 (1993). Although not suggested previously, it is expected that an antibody directed against (and blocking) a glutamate receptor in particular (a defined antigen) contributes to some forms of schizophrenia. This is expected because: (1) drugs such as phencyclidine that block the NMDA receptor produce psychotic symptoms in otherwise normal individuals and can precipitate a recurrence of schizophrenia in patients with latent schizophrenia; and (2) the findings in Rasmussen's encephalitis demonstrate the precedence for an auto-immune process directed against a glutamate receptor.

While the methods of the present invention are intended for application to human subjects, they may also be applied to animal subjects (e.g., horse, dog, cat) for veterinary medical purposes, including (but not limited to) the treatment of seizure disorders. Subjects to be screened by the methods of the present invention include subjects which have not previously been diagnosed as being afflicted with a CNS disorder for the purpose of making an initial diagnosis, or subjects who have previously been diagnosed as afflicted with a CNS disorder, either for confirming that diagnosis or monitoring ongoing treatments as discussed below.

Glutamate receptors with which the methods of the present invention are concerned include both ionotropic and metabotropic glutamate receptors. Glutamate receptors are categorized by their most selective agonists. Thus, examples of ionotropic glutamate receptors include, but are not limited to, NMDA (N-methyl-D-aspartate), KA (kainate), AMPA (alpha-amino- 3-hydroxy-5-methyl-4-isoxazole propionate) receptors, and examples of metabotropic glutamate receptors include, but are not limited to, L-AP4 (2-amino-4-phosphonobutyrate) and ACPD (trans-1-amino-cyclopentane-1,3-dicarboxylate) receptors. See generally G. Gasic and M. Hollmann, *Ann. Rev. Physiol.* 54, 507 (1992). Subtypes thereof are included herein, such as, for example, the GluR1, GluR2, GluR3, and GluR4 subtypes of the AMPA receptor, and the GluR5, GluR6, and GluR7 subtypes of the KA receptor. Where glutamate receptor (including antigenic fragments thereof such as the extracellular domain) is used in carrying out the methods described herein, it may be of the same species or different species of origin of the subject undergoing screening or treatment (i.e., human, dog, bovine, rat), but is typically mammalian in origin. The glutamate receptor may be produced by purification from natural sources or may be produced by recombinant means.

Any antibody-containing biological sample may be collected from the subject and employed in carrying out the present invention, including blood, blood serum, blood plasma, cerebrospinal fluid, and brain tissue. The sample may be collected in the course of withdrawing blood for carrying plasmapheresis or the like, a sample may be collected by venipuncture or lumbar puncture, the sample may be a tissue biopsy during surgery, or the sample may be collected by any other suitable means.

The detecting step in the present invention may be carried out by any suitable immunoassay, including homogeneous assays or heterogeneous assays. Examples of suitable immunoassays include, but are not limited to, radioimmunoassay, immunofluorescence assay, enzyme-linked immunosorbent assay (ELISA), immunocytochemical assay, and immunoblotting.

In a typical assay, the reagents are usually the specimen, the antibody to be detected, and means for producing a detectable signal. Specimens as described above may be used. The antigen (glutamate receptor as described above) is generally immobilized on a support, such as a bead, plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the antibody in the specimen. Means for producing a detectable signal include the use of radioactive labels, fluorescent labels, enzyme labels, and so forth. For example, an antibody which binds to the antibody to be detected (e.g., goat anti-human immunoglobin) can be conjugated to a detectable group and added to the liquid phase reaction solution before the separation step. The presence of the detectable group on the solid support indicates the presence of the antigen in the test sample.

Those skilled in the art will be familiar with numerous specific immunoassay formats and variations thereof which may be useful for carrying out the detection step disclosed herein. See generally E. Maggio, *Enzyme-Immunoassay*, (1980)(CRC Press, Inc., Boca Raton, Fla.); R. Nakamura et al., *Enzyme Immunoassays: Heterogeneous and Homogeneous Systems*, In Handbook of Experimental Immunology, Vol. 1, chap. 27 (D. M. Weir ed. 1986)(Blackwell Scientific Publications) , see also U.S. Pat. No. 4,727,022 to Skold et al., U.S. Pat. No. 4,659,678 to Forrest et al., U.S. Pat. No. 4,376,110 to David et al., U.S. Pat. No. 4,275,149 to Litman et al., U.S. Pat. No. 4,233,402 to Maggio et al., and U.S. Pat. No. 4,230,767 to Boguslaski et al. Applicants specifically intend that the disclosures of all U.S. Patent references cited herein be incorporated herein by reference.

Diagnostic kits for carrying out the methods disclosed above may be produced in a number of ways. In one embodiment, the diagnostic kit comprises (a) an glutamate receptor protein conjugated to a solid support and (b) a second anti-human antibody of the invention conjugated to a detectable group (e.g., a detectable group as described above). The reagents may also include ancillary agents such as buffering agents and protein stabilizing agents, e.g., polysaccharides and the like. The diagnostic kit may further include, where necessary, other members of the signal-producing system of which system the detectable group is a member (e.g., enzyme substrates), agents for reducing background interference in a test, control reagents, apparatus for conducting a test, and the like. A second embodiment of a test kit comprises (a) a glutamate receptor antigen, and (b) a specific binding partner for the antigen conjugated to a detectable group. Ancillary agents as described above may likewise be included. The test kit may be packaged in any suitable manner, typically with all elements in a single container along with a sheet of printed instructions for carrying out the test.

The amount of anti-glutamate receptor autoantibody available to bind to glutamate receptors in a subject may be reduced by any suitable means. For example, the autoantibody level may be reduced by plasmapheresis (the removal of blood from the subject, separation of the plasma from blood cells, and reinjection of the cells). In particular embodiments, plasmapheresis may be carried out by plasma exchange (where the plasma removed is replaced in whole or in part by a plasma substitute such as lactated Ringer's solution) or by plasma perfusion (where the autoantibodies are separated from the plasma and the plasma then returned to the patient). Any suitable apparatus may be employed, including, but not limited to, centrifugal devices such as the Haemonetics Model 30 blood processor, the IBM 2997 blood processor, and the Fenwall Laboratories CS-3000 blood cell separator, and plasma filter membrane devices such as the Cobe Centry TPE module.

Autoantibodies may be removed from the patient's plasma by any suitable technique, such as by contacting the plasma to a solid support having an immunoglobulin binding protein (e.g., protein A) immobilized thereon, removing the plasma from the solid support, and then returning the plasma to the patient. Typically, this method is practiced by immobilizing the immunoglobulin binding protein on an affinity support in an affinity column, passing the blood plasma through the affinity column, and returning the plasma to the patient (optionally, but preferably, recombining the plasma with the patient's blood cells). The method may also be carried out on whole blood or other suitable blood fraction, which may then be recombined with blood cells and then returned to the patient, as will be appreciated by persons skilled in the art. See, e.g., U.S. Pat. No. 3,996,898 to Sjoquist and Sjodin, U.S. Pat. No. 3,995,018 to Sjoquist, and U.S. Pat. No. 5,128,451 to Allen.

In a variation of the foregoing, glutamate receptor or an antigenic fragment thereof may be immobilized on the solid support, and the anti-glutamate receptor autoantibodies selectively removed from the patient's blood by contacting the patient's blood, blood plasma, or other suitable fraction to the solid support, as described above. Such procedures advantageously avoid substantial reduction in levels of other antibodies in the subject undergoing treatment.

The volume of the plasma removed from the patient during each plasmapheresis treatment will vary depending on the age, weight, and condition of the subject, and on whether that volume is being returned to the subject or replaced with a suitable substitute. Typically, the volume of plasma removed will be from one-half liter to three liters per treatment. One or more plasmapheresis treatments may be carried out each day (e.g., two to three per day), and plasmapheresis may be carried out once, twice, or three or more times per week, again depending on conditions such as noted above. Higher volumes may be removed when treatment is first initiated, and higher volumes may be removed when anti-glutamate receptor autoantibodies are being selectively removed from the patient's blood and that blood returned to the patient, as discussed above.

An alternative method for reducing antibodies available to bind glutamate receptors in the subject is by administering anti-idiotypic antibodies to the subject, which anti-idiotypic antibodies bind to the combining region of said autoantibodies. The administering step may be carried out by any suitable means, including by intraveneous, intramuscular, or subcutaneous injection. Anti-idiotypic antibodies may be produced in accordance with known techniques. The anti-idiotypic antibodies may be "humanized" antibodies, i.e., a sufficient portion thereof being human in origin to minimize an immune reaction thereto in the subject, such as described in PCT Patent Application WO92/15683 and PCT Patent Application WO92/15699. The quantity of anti-idiotypic antibody administered may be determined from the titer or amount of the autoantibody present in the subject, which may be determined by the assay procedures described above.

Oral tolerance, a classic technique for inducing immune tolerance (see, e.g., H. Weiner, *Science* 259, 1321 (1993); M. Chase, *Proc. Soc. Exp. Biol. Med.* 61, 257 (1946); H. Wells, *J. Infect. Dis.* 9, 147 (1911)), may also be employed to reduce the amount of anti-glutamate receptor autoantibodies in the subject which are available to bind to glutamate receptors. Such techniques may involve orally administering to the subject an active agent comprising a glutamate receptor protein as described above, or an antigenic fragment thereof or fusion protein of either thereof. This produces an alteration of the immune response to the antigen which may suppress a previous immune response to that antigen. The glutamate receptor protein may be of any mammalian origin (e.g., bovine, monkey), but is preferably of human origin. An immune adjuvant (e.g., a lipopolysaccharide) may optionally be administered concurrently with the antigen.

Depending on the species and nature of active agent, whether or not an adjuvant is administered, the condition of the subject, and the schedule of administration, the oral dosage of the active agent may be administered in any amount effective to achieve oral tolerance. A non-limiting example of dosage is from about 10 or 20 mg up to about 500 or 1000 mg. The dosage may be administered in accordance with any suitable schedule, such as one, two, or three times daily.

Formulations useful for carrying out oral tolerance treatments as described above comprise an active agent as described above, typically in combination with an orally administrable carrier, in an orally administrable form. Orally administrable formulations may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier. In general, the formulations of the invention are prepared by uniformly and intimately admixing the active compound with a liquid or finely divided solid carrier, or both, and then, if necessary, shaping the resulting mixture.

For example, a tablet may be prepared by compressing or molding a powder or granules containing the active agent, optionally with one or more accessory ingredients such as an immune adjuvant.

In practice, the amount of anti-glutamate receptor autoantibodies in the patient available to bind to glutamate receptor will be monitored, such as by the procedures described above, on a repeated basis to monitor the progression or state of the disease, or effectively carry out a therapeutic treatment such as described above. This may be carried out by collecting the biological sample at intervals of from about one week to one month, preferably weekly, from the subject, so that the increase or decrease in autoantibody levels in the subject over time may be seen. A decrease in the autoantibodies indicates improvement or a possibility of improvement in the disease, and an increase in the autoantibodies indicates progression or risk of progression of the disease. Typically, where monitoring is carried out in conjunction with a treatment of the disease, at least one measure will be taken from the subject to confirm the autoimmune basis of the disorder prior to initiating treatment, and preferably several measures will be taken to establish a baseline titer or amount of the autoantibody in the subject. The antibody measure is then to be taken at least periodically after the therapeutic intervention, and the condition of the patient monitored by standard clinical indices, to determine the efficacy of the therapeutic treatment and adjust the treatment to enhance the efficacy thereof.

The present invention is explained in greater detail in the following non-limiting Examples.

EXAMPLE 1

Development of a Rabbit Model for Rasmussen's Encephalitis

In the course of raising antisera to various glutamate receptors in rabbits for other reasons, we unexpectedly developed an animal model for Rasmussen's encephalitis. In brief, antisera was prepared in rabbits to a bacterially expressed portion of the extracellular domain of glutamate receptors (GluRs) 1 through 6. All rabbits produced high titer, subunit specific antibodies to the injected antigen. During the course of preparing these antisera, 2 rabbits injected with the bacterial fusion protein containing a GluR3 extracellular domain developed anorexia, bizarre behavior and repetitive movements consistent with seizures subsequent to the third boost. Pair rabbits injected with related fusion proteins expressing GluR1, GluR2, GluR5, or GluR6, respectively, failed to develop abnormal behavior or seizures.

The brains of the two rabbits immunized with the GluR3 fusion protein were examined and showed similar inflammatory neuropathologic features. Gross examination was unremarkable. Microscopic examination showed a mild diffuse lymphocytic infiltrate in the leptomeninges. Perivascular cuffing was present primarily in the neocortex and olfactory cortex, but was also noted in the hippocampus and caudate nucleus. Microglial nodules were frequent in the outer layers of the neocortex (primarily in layer II and the junction of layers I and II) and olfactory cortex. Rare microglial nodules were observed in the hippocampus and the cerebellum. None were observed in the basal ganglia, thalamus or brainstem.

The inflammatory changes were distributed in a pattern coincident with the distribution of the GluR3 in the rat brain. Since these inflammatory abnormalities occurred in rabbits immunized with GluR3 (fraction thereof), it was considered likely they represent an immune-mediated response directed against GluR3. In addition, it was observed that these neuropathologic findings bear great similarity to the characteristic inflammatory neuropathologic abnormalities found in Rasmussen's encephalitis.

EXAMPLE 2

Immunoblotting Assay for Detecting Anti-Glutamate Receptor Autoantibodies

Glutamate receptor fusion protein constructs with TrpE, overproduction of protein in bacteria, fractionation by SDS-PAGE, and Western blot analysis were done in accordance with known techniques as described in S. Rogers et al., *J. Neurosci.* 11, 2713 (1991) and S. Rogers et al., *J. Neurosci.* 12, 4611 (1992). Each Western blot was blocked with freshly prepared 2 percent dry milk in phosphate buffered saline (blotto) for 1 hour at room temperature, and then rocked in blotto with serum from sample diluted 1:100 overnight at 4° C. Blots were then rocked at room temperature for 2 hours, rinsed in PBS 4 times over a period of one hour, and returned to blotto containing goat anti-human IgG alkaline phosphatase at 1:750 for one hour at room temperature. Blots were again rinsed in PBS as before, then rinsed in 50 mM TRIS, 100 mM NaCl, and 2 mM $MgCl_2$ twice (developing buffer). Immunoreactivity was visualized by placing the blots in developing buffer containing one μg/ml nitro blue tetrazolium and 0.5 μg/ml BCIP (5-Bromo-4-Chloro-3-Indolyl Phosphate) (Rogers et al., supra (1992)). The following was done to remove irrelevant immunoreactivity towards background bacterial proteins. *Escherichia coli* NM522 cells were grown for 14 hours at 37° C. in YT nutrient broth, harvested by centrifugation, rinsed with 10 mM Tris buffer, pH 7.2, and lysed by repeated freeze thawing. A suspension of lysed bacteria was then added to the serum sample, rocked for 2 hours at room temperature, centrifuged at 13,000×g for 10 minutes, and the supernatant was then used for Western blot analysis as described above.

EXAMPLE 3

Immunocytochemical Assay for Detecting Anti-Glutamate Receptor Autoantibodies

Human embryonic kidney 293 cells were transfected with expression plasmids containing either the cDNA for GluR3 (G. Huntley et al., *J. Neurosci.* 13, 2965 (1993)) or the bacterial protein beta-galactosidase, fixed with paraformaldehyde, permeabilized with Triton X-100, and reacted with serum in accordance with known techniques (see Huntley et al., supra). Typical serum dilutions for an immunized rabbit was 1:2000 and 1:1000 for human sera. The serum from one Rasmussen's encephalitis patient exhibited a strong nuclear immunoreactivity. Due to this, immune diluted serum samples were absorbed against non-transfected 293 cells in accordance with known techniques (Rogers et al., supra (1992); Huntley et al., supra).

EXAMPLE 4

Enzyme-Linked Immunosorbent Assay for Detecting Anti-Glutamate Receptor Autoantibodies ELISA was carried out essentially in accordance with known techniques (Rogers et al., supra (1992)). Overproduced proteins (trpE fusion proteins with GluR3 or neuronal nicotinic acetylcholine receptor subunit β4 as a background control) were dissolved in freshly prepared 8 M urea (10 ml per gram of protein) for one hour at room temperature, centrifuged, and the supernatant diluted 10 fold by the slow addition of a solution of 50 mM KCl and 50 mM NaCl (pH 10.5). The solution was brought to pH 8 with 1 N HCl and repeatedly dialyzed against 10 mM NaCl in 10 mM sodium phosphate buffer (pH 7.2) at 4° C. and the protein concentration determined using a BioRad protein assay kit. To prepare IMMULON™ microtiter plates, antigen (0.2 μg/well) in 50 μl of phosphate-buffered-saline (PBS) was added to each well for 14 hours at 4° C. Wells were thoroughly washed with blocking PBS (PBS containing 2 percent dry nonfat milk) for 1–2 hours at room temperature. Serum at various dilutions (e.g., 1:5, 1:50, 1:250) in blocking PBS was then added, and dishes were incubated for 1 hour at room temperature. Plates were washed 5 times with blocking PBS before adding goat-anti human IgG alkaline phosphatase coupled second antibody (1:7500) for 45 minutes at room temperature. Plates were washed with PBS and developed with 2,2'-azino-di- 3-ethylbenzthiazoline-6-sulfonic acid (1 mg/ml) in McIlvain's buffer (pH 4.6) and 0.0005% hydrogen peroxide. The plates were scanned on a TERITEK™ multiscan ELISA reader and the values for nicotinic acetylcholine receptor β4 fusion protein were subtracted from GluR3 fusion protein to produce a GluR3-specific reading.

EXAMPLE 5

A Survey of Glutamate Receptor Autoantibodies in Patients Afflicted with Rasmussen's Encephalitis To test the hypothesis that an autoimmune process directed against GluR3 is associated with Rasmussen's encephalitis, the prevalence of GluR3 Ab was surveyed. The sera from four patients with pathologically-confirmed Rasmussen's encephalitis, four age and sex matched epileptic children, four other epileptic children, four age and sex matched normal children, and four other normal children were examined for immunoreactivity towards GluR3 and other closely related glutamate receptors using Western blot analysis as described in Example 2 above and tranfected cells expressing GluR3 as described in Example 3 above. As shown in Table 1, sera from two of the four patients with Rasmussen's encephalitis (JH, JS) showed positive immunoreactivity to GluR3 fusion protein and one of the remaining two patients with Rasmussen's encephalities (CF) intermittently showed weak immunoreactivity to GluR2 fusion protein by Western Blot analysis, whereas only one of the sixteen control patients' sera showed immunoreactivity to GluR3 or any of the other fusion proteins (GluR1, GluR2, GluR4, GluR5 or nAChR). Three of the four patients with Rasmussen's encephalitis (JH, JS, CF) showed immunoreactivity to transfected cells expressing GluR3. None of these three showed immunoreactivity to transfected cells expressing the related glutamate receptor subunits GluR1 or GluR6. None of the sixteen controls exhibited immunoreactivity to GluR3 expressed in transfected cells.

TABLE 1

Survey of Anti-Glutamate Receptor Antibodies in Various Patients.

| DIAGNOSIS | IMMUNOREACTIVITY | |
|---|---|---|
| | Western Blot | Transfected Cells |
| RASMUSSEN PATIENTS | | |
| JH: Progressive | GluR3 | GluR3 |
| JS: Progressive | GluR3/GluR2 | GluR3 |
| CF: Stable; few Sz | weak GluR2 | GluR3 |
| AT: Stable; few Sz | none | none |
| AGE AND SEX MATCHED EPILEPTIC CONTROLS | | |
| Absence + GM SZ | none | none |
| Focal Sz 2d to Stroke | none | none |
| Complex partial Sz | none | none |
| Post-traumatic Sz | none | none |
| AGE AND SEX MATCHED NORMAL CONTROLS | | |
| Cardiac surgery | GluR3 | none |
| trauma | none | none |
| trauma | none | none |
| obesity | none | none |
| 4 EPILEPTIC CHILDREN | none | none |
| 4 NORMAL CHILDREN | none | none |

Amongst the patients with Rasmussen's encephalitis, those with active, progressive disease (JH, JS) showed the most immunoreactivity to GluR3 by Western blot analysis and with transfected cells expressing GluR3. The patient who was intermittently weakly reactive to GluR2 fusion protein and not to GluR3 fusion protein by Western blot analysis, but showed surface immunoreactivity to transfected cells expressing GluR3 (CF) had stable severe unihemispheric dysfunction and infrequent seizures. The only patient with Rasmussen's encephalitis who did not show immunoreactivity to any of the GluR fusion proteins by Western blot analysis or transfected cells expressing GluR3 (AT) had undergone hemispherectomy two year previously and had remained clinically stable and seizure-free since. These observations indicate a link between on-going seizures, active encephalitis and expression of the GluR3 Ab. They also indicate that the immune response directed against GluR3 may eventually subside, which correlates with the long term outcome observed in patients with Rasmussen's encephalitis, who after progression over months or years, eventually stabilize spontaneously.

The control patient who showed immunoreactivity to GluR3 fusion protein by Western analysis had been tested one week after open heart surgery for mitral valve disease. She did not show antibody binding to transfected cells expressing GluR3. The significance of this is uncertain, but several factors may be involved. Cardiac bypass under hypothermic anesthesia is a nonspecific activator of the immune system and may have enhanced nonspecific cross-reactivity to the bacterially expressed GluR3 fusion protein; and the configuration of the GluR3 antigen expressed on Western blot may be different from the three dimensional configuration of GluR3 expressed in transfected cells or neurons, with subsequent selection of antibodies with slightly different affinities.

EXAMPLE 6

Therapeutic Treatment of Rasmussen's Encephalitis by Removal of Glutamate Receptor Autoantibodies Patient J. S. from example 5 above, a human female nine years of age, was well until age six, when she struck her left forehead. Since that time she has suffered increasingly frequent, intractable generalized and right focal seizures with progressive cognitive decline and profound speech disability. Neuroimaging showed progressive left hemisphere atrophy. Neuropathologic examination of a left hemisphere biopsy confirmed the diagnosis of Rasmussen's encephalitis. Defunctioning hemispherectomy would have been the next conventional therapeutic option. Removal of the antibody to GluR3 by recurrent plasma exchange (PEX) was accordingly carried out as a treatment.

Prior to PEX she was persistently lethargic and almost mute. She could understand only one or two step commands and was unable to read or write or perform simple math such as 2+2. She had right visual field neglect and mild right hemiparesis. As shown in FIG. 1, she suffered about 12 seizures daily.

She was treated with recurrent, single-volume PEX (seven treatments in the first three weeks and single weekly thereafter), without change in dosage or trough levels of her anticonvulsant medications. PEX was carried out by the removal of 1200 milliliters of plasma using a COBE Spectra apparatus. This volume was replaced with lactated Ringer's solution containing 5% human albumin. Her blood was anticoagulated by addition of acid citrate dextrose (ACD) at a ratio of approximately 12:1; blood:ACD.

After PEX, the subject displayed a rapid, dramatic, beneficial response to PEX. During the first six to seven weeks, seizure frequency decreased by 80% (see FIG. 1), she began to speak spontaneously using simple words and phrases, her understanding improved, her right hemiparesis improved, and, for the first time in two years, she resumed playing with dolls, riding a bicycle and spontaneously participating in household activities. Some evidence of her improved writing and drawing were observed, and she was able to correctly perform simple math such as 3+5 and 4–2. Over the next four weeks of the study, however, seizure frequency slowly increased and cognitive and motor skills deteriorated. As also shown in FIG. 1, these initial clinical improvements and subsequent deterioration closely paralleled the initial decrease and subsequent rise in circulating anti-GluR3 Ab levels.

The foregoing is illustrative of the present invention, and not to be construed as limiting thereof. The invention is defined by the following claims, with equivalents of the claims to be included therein.

That which is claimed is:

1. A method of screening a subject for an active central nervous system disorder, comprising:

collecting a biological sample from said subject; and then detecting the presence or absence of anti-glutamate receptor autoantibodies in said biological sample, the presence of said autoantibodies indicating said subject is afflicted with or at risk of developing a central nervous system disorder caused by autoimmune disease, and wherein said detecting step comprises detecting the presence or absence of autoantibodies that specifically bind to an ionotropic glutamate receptor.

2. A method according to claim 1, wherein said biological sample is a biological fluid.

3. A method according to claim 1, wherein said biological sample is selected from the group consisting of blood, blood plasma, blood serum, cerebrospinal fluid, and brain tissue.

4. A method according to claim 1, wherein said central nervous system disorder is a seizure disorder.

5. A method according to claim 1, wherein said central nervous system disorder is an inflammatory disorder.

6. A method according to claim 1, wherein said central nervous system disorder is temporal lobe epilepsy with inflammatory pathologic changes of the temporal lobe.

7. A method according to claim 1, wherein said central nervous system disorder is Rasmussen's encephalitis.

8. A method according to claim 1, wherein said central nervous system disorder is amyotrophic lateral sclerosis.

9. A method according to claim 1, wherein said detecting step comprises detecting the presence or absence of autoantibodies that specifically bind to an ionotropic glutamate receptor selected from the group consisting of NMDA, KA, and AMPA glutamate receptors.

10. A method according to claim 1, wherein said detecting step comprises detecting the presence or absence of autoantibodies that specifically bind to an AMPA glutamate receptor.

11. A method according to claim 1, wherein said subject has not previously been diagnosed as afflicted with a central nervous system disorder.

12. A method according to claim 1, wherein said subject has previously been diagnosed afflicted with a central nervous system disorder.

13. A method of monitoring an active disease of the central nervous system in a subject afflicted with such disease, comprising:

(a) collecting a biological sample from said subject; then (b) detecting the amount of anti-glutamate receptor autoantibodies in said biological sample, and wherein said detecting step comprises detecting the presence or absence of autoantibodies that specifically bind to an ionotropic glutamate receptor; and then (c) repeating step (a) and (b) above to determine a change in anmount of autoantibodies in said sample, a decrease in amount indicating an improvement in said disease and an increase in said amount indicating the progression of said disease.

14. A method according to claim 13, wherein said subject is concurrently undergoing treatment for said disease.

15. A method according to claim 13, wherein said collecting step is repeated at an interval of about one week to one month.

* * * * *